United States Patent
Young

(10) Patent No.: US 10,702,325 B2
(45) Date of Patent: Jul. 7, 2020

(54) PLASTICS IMPLANT REVISION AND REMOVAL SYSTEM

(71) Applicant: RADLEY SCIENTIFIC LIMITED, South Devon (GB)

(72) Inventor: Michael John Radley Young, South Devon (GB)

(73) Assignee: RADLEY SCIENTIFIC LIMITED, South Devon (GB)

(*) Notice: Subject to any disclaimer, the term of this patent is extended or adjusted under 35 U.S.C. 154(b) by 467 days.

(21) Appl. No.: 15/326,527

(22) PCT Filed: Jul. 20, 2015

(86) PCT No.: PCT/GB2015/000216
§ 371 (c)(1),
(2) Date: Jan. 16, 2017

(87) PCT Pub. No.: WO2016/009167
PCT Pub. Date: Jan. 21, 2016

(65) Prior Publication Data
US 2017/0202590 A1    Jul. 20, 2017

(30) Foreign Application Priority Data

Jul. 18, 2014  (GB) .................................. 1412833.4
Sep. 13, 2014  (GB) .................................. 1416208.5

(51) Int. Cl.
*A61B 17/92* (2006.01)
*A61B 17/16* (2006.01)
(Continued)

(52) U.S. Cl.
CPC .......... *A61B 17/921* (2013.01); *A61B 17/164* (2013.01); *A61B 17/3423* (2013.01);
(Continued)

(58) Field of Classification Search
CPC ..... A61B 17/92; A61B 17/921; A61B 17/164; A61B 17/320068; A61B 17/3472; A61B 17/8847
(Continued)

(56) References Cited

U.S. PATENT DOCUMENTS 5,045,054 A * 9/1991 Hood ................. A61B 17/8847
604/22
5,151,099 A * 9/1992 Young .............. A61B 17/22012
606/169
(Continued)

FOREIGN PATENT DOCUMENTS

CN      202875463 U    4/2013
EP       2640291 A1    9/2013
(Continued)

OTHER PUBLICATIONS

International Search Report and Written Opinion issued in PCT/GB2015/000216, dated Jan. 4, 2016.

*Primary Examiner* — Matthew J Lawson
(74) *Attorney, Agent, or Firm* — Heslin Rothenberg Farley & Mesiti P.C.; Stephen P. Scuderi

(57) ABSTRACT

A fracture in a hollow bone is supported temporarily by a rigid plastics implant formed within a balloon within the bone. To assist implant removal, an access port, comprising a hollow cylinder, is inserted through an aperture made in an end of the bone and surrounds a proximal end of the implant. The access port is connected to a source of torsional-mode ultrasonic vibrations to soften the plastic implant and improve engagement between access port and implant. Removal of the ultrasound source allows introduction of a cutting tool through the access port, which guides it to hollow out the implant. The implant then collapses within the balloon and is withdrawn through the access port. One suitable cutting tool has a head with four helical fins
(Continued)

separated by part-circular grooves and a concave distal face. Ultrasonically activated, the fin tips soften and cut the plastic, which flows away along the grooves.

18 Claims, 2 Drawing Sheets

(51) Int. Cl.
  *A61B 17/88* (2006.01)
  *A61B 17/34* (2006.01)
  *A61B 17/32* (2006.01)
  *A61B 17/17* (2006.01)
  *A61B 17/72* (2006.01)

(52) U.S. Cl.
  CPC ...... *A61B 17/3472* (2013.01); *A61B 17/8847* (2013.01); *A61B 17/8863* (2013.01); *A61B 17/1615* (2013.01); *A61B 17/1631* (2013.01); *A61B 17/17* (2013.01); *A61B 17/7275* (2013.01); *A61B 2017/320089* (2017.08)

(58) Field of Classification Search
  USPC .......................................................... 606/291
  See application file for complete search history.

(56) References Cited

U.S. PATENT DOCUMENTS

| | | | | |
|---|---|---|---|---|
| 5,330,481 | A * | 7/1994 | Hood | A61B 17/8847 128/898 |
| 5,382,251 | A * | 1/1995 | Hood | A61B 17/8847 606/2 |
| 5,499,986 | A * | 3/1996 | Dimarco | A61B 17/921 606/104 |
| 5,749,877 | A * | 5/1998 | Young | A61B 17/8847 128/898 |
| 2014/0277028 | A1* | 9/2014 | Voic | A61B 17/320068 606/169 |

FOREIGN PATENT DOCUMENTS

| | | |
|---|---|---|
| FR | 2237609 A1 | 2/1975 |
| WO | 1993003676 | 3/1993 |
| WO | 1996020657 | 7/1996 |
| WO | 2012068172 A1 | 5/2012 |
| WO | 2013013071 A1 | 1/2013 |

* cited by examiner

PLASTICS IMPLANT REVISION AND REMOVAL SYSTEM

The present invention relates to apparatus for use in the revision and removal of orthopaedic prostheses, especially intraosteal prostheses. More particularly but not exclusively, it relates to ultrasonically-vibratable apparatus for improving access to intraosteal prostheses for revision and removal; and also to an ultrasonically-vibratable tool head for removing polymers from within bone cavities and for trimming bone during the implantation, revision or removal of intraosteal prostheses including trauma/fracture fixation procedures.

A common medical requirement is to support a fractured bone during healing, to reduce the chances of a reduced fracture becoming misaligned or the chances of a partially-healed fracture being broken again. A relatively recent development in this field is described in International Patent Application No. WO2013/013071 and other applications from the same proprietor. In this invention, a fractured hollow long bone is supported by an internally-formed plastics prosthesis or implant extending within the bone across the fracture.

In outline, a window is opened through an end surface of the bone into the hollow interior or medullary cavity of the bone. A portion of the marrow is removed and replaced with an elongate balloon structure, which is inflatable to push displaced bone elements into alignment from within, thus reducing the fracture. For long term support, a photopolymerisable liquid is introduced into the balloon, followed by an elongate light guide, extending generally longitudinally of the balloon. Light of a frequency appropriate to polymerise the liquid is passed along the light guide to polymerise the liquid into the form of a rigid plastics body extending within the medullary cavity, across the site of the fracture. The light guide is then withdrawn. This rigid internal plastics implant thus supports the bone during the healing process.

In orthopaedic surgery, there is a general principle that prostheses and other implants should not be implanted into the body unless a procedure is available for their removal, either once a temporary implant has outlived its usefulness or as part of a revision procedure, if a prosthesis has failed for any reason. It is hence a general object of the present invention to provide means to simplify the removal of such prostheses and implants.

The currently preferred approach is to introduce a tool through the window at the end of the bone and to use the tool to core out plastics material from the implant by passing the tool down a generally longitudinal region of the implant. When a sufficient proportion of the rigid plastics material has been extracted, the now hollow implant will collapse inwardly. The balloon, containing the collapsed remains of the implant, can then be drawn out through the window.

Two problems have arisen with this approach. Firstly, it is difficult to ensure that the tool to core out ("debulk") the implant is passed substantially down a longitudinal axis of the prosthesis, rather than veering to one side and possibly penetrating the balloon or even contacting an internal surface of the wall of the bone. Secondly, it can be difficult to grasp a proximal end of the balloon and/or the implant so as to draw it out of the medullary cavity.

It is hence an object of the present invention to provide apparatus for use during removal or revision of an internal rigid plastics implant that improves the accuracy of removal of plastics material from the axial region of the implant and/or aids engagement with the implant to simplify its extraction. It is further an object of the present invention to provide an improved method for removal or revision of an internal rigid plastics implant from within a bone cavity, using such apparatus.

A further issue with such procedures is the selection of a suitable tool for the debulking of the implant. It is known that ultrasonically-activated instruments are of use in the removal of poly(methyl methacrylate) (PMMA) bone cement in joint revision arthroplasty. PMMA has a depolymerisation/softening temperature of around 120° C., which allows the heating effect of ultrasonic vibrations from the instrument to weaken and soften cement remaining in the medullary cavity of a bone after implant removal. Examples of such instruments are shown in International Patent Applications Nos. WO93/03676 and WO96/20657, amongst numerous others. Such prior art instruments teach particular operative features, particularly of their distally-located operative heads, which for example facilitate collection of the softened cement for removal from the cavity.

It is also known for careful design of the acoustic system, which has traditionally been based on longitudinal-mode ultrasonic activation, differentially to energise the PMMA cement whilst avoiding heating the cortical bone during accidental transitory contact between the activated operative head or probe tip and the bone.

However, longitudinal-mode ultrasonic vibrations have been found to have shortcomings. The typical elongate surgical instrument, energised with longitudinal-mode ultrasonic vibrations, has a characteristic distal extensional drilling effect on any material, including body tissues, with which it is in axial contact. This provides an inevitable threat of bone penetration and damage with the distal head/tip of the tool. Longitudinal-mode ultrasonic vibrations impose other functional and structural constraints on tools relying on them, which make existing instruments less than ideal.

There are also other polymeric materials coming into surgical use, such as fracture fixation using polymers cured in situ using ultraviolet irradiation. These polymers are less susceptible to softening and removal using the known instruments described above.

There is also frequently a need to trim bone within a cavity, such as during revision procedures, particularly where cancellous bone structures have grown within a bone cavity or between an implant and the adjacent cortical bone, while the implant was in place. Cortical bone may also need reshaping to receive a new implant. It would therefore be convenient if a common tool head could be used to remove both plastics materials and bone.

It is hence another object of the present invention to provide an operative head for a surgical tool, and a surgical tool comprising such an operative head, that obviate the above problems of existing surgical tools and permit faster and safer removal of a wider range of plastics materials and even bone, particularly in conjunction with the use of alternative modes of ultrasonic vibrations.

According to a first aspect of the present invention, there is provided an access port device for insertion into a bone to aid revision of an internal plastics implant extending within a cavity of said bone, comprising a hollow cylindrical body extending longitudinally from a proximal to a distal end, wherein the hollow cylindrical body is mountable adjacent its proximal end to a source of ultrasonic vibrations, and a distal portion of the hollow cylindrical body is insertable through an aperture formed in the bone into the cavity of the bone, to extend around a proximal portion of the implant, with a longitudinal axis of the hollow cylindrical body being substantially coaxially aligned with a longitudinal axis of the implant.

Preferably, said distal portion of the hollow cylindrical body extends between said proximal portion of the implant and an adjacent inner surface of the cavity.

Advantageously, an inner surface of said distal portion of the hollow cylindrical body is profiled to engage with the plastics material of the implant.

Said inner surface may be provided with screw thread means.

Optionally, said distal portion of the hollow cylindrical body may taper towards the distal ends of the hollow cylindrical body.

Said tapering may comprise an outer surface of the hollow cylindrical body alone, an inner surface thereof having a constant diameter, such that the walls of the hollow cylindrical body taper towards its distal end.

Preferably, the access port device comprises a metal, advantageously titanium.

Preferably, the hollow cylindrical body is provided at its proximal end with engagement means by which it may detachably be mounted to the source of ultrasonic vibrations.

Advantageously, said engagement means comprises screw thread means extending around an outer surface of the hollow cylindrical body adjacent its proximal end, adapted to engage with cooperating screw thread means on the source of ultrasonic vibrations.

Preferably, the access port means is so dimensioned that an antinode of the ultrasonic vibrations is located adjacent the distal end of the hollow cylindrical body.

According to a second aspect of the present invention, there is provided a tool for inserting an access port device into a bone to aid revision of an internal plastics implant extending within a cavity of the bone, comprising an access port device as described in the first aspect above detachably mounted to a source of ultrasonic vibrations.

Preferably, said source of ultrasonic vibrations comprises a source of torsional-mode ultrasonic vibrations.

Advantageously, said source of ultrasonic vibrations comprises a stack of piezo-electric elements mounted to a conversion horn means, the access port device being mountable to the conversion horn means, either directly or by way of elongate waveguide means.

The access port device may be mounted to the source of ultrasonic vibrations by screw thread means.

The tool may be so configured and dimensioned that an antinode of the ultrasonic vibrations is located adjacent the distal end of the hollow cylindrical body of the access port device.

According to a third aspect of the present invention, there is provided a method for revising an internal plastics implant extending within a cavity of a bone, comprising the steps of providing an access port device as described in the first aspect above; mounting it to a source of ultrasonic vibrations; inserting a distal portion of the hollow cylindrical body of the access port device through an aperture formed in the bone so that it extends around a proximal portion of the implant, with a longitudinal axis of the hollow cylindrical body being substantially coaxially aligned with a longitudinal axis of the implant; and passing cutting tool means through the hollow cylindrical body and aligned therewith, so as to remove plastics material from a generally axial region of the implant.

Preferably, during said insertion of the access port device, the source of ultrasonic vibrations is operated to cause the hollow cylindrical body of the access port device to vibrate ultrasonically, thus softening adjacent plastics material of the implant to facilitate said insertion.

Advantageously, following said insertion, the source of ultrasonic vibrations is inactivated and detached from the access port device.

The access port device preferably then remains engaged with the proximal portion of the implant.

The access port device may then be employed, following the removal of plastics material from within the implant, to pull a remainder of the implant out of the cavity in the bone.

According to a fourth aspect of the present invention, there is provided an operative head for an ultrasonically-activatable surgical tool, comprising an elongate body of generally cylindrical symmetry comprising at least three elongate radially-outstanding helical fin means, each extending between a proximal end and a distal end of the elongate body, said fin means being defined by a corresponding number of helically-extending groove or slot means, also extending between said proximal and distal ends. Preferably, said fin means taper in width, being broader adjacent the proximal end of the elongate body than adjacent its distal end.

Each fin means may have a width adjacent said proximal end that is between 50% and 100% greater than its width adjacent said distal end.

Preferably, said groove or slot means are deeper adjacent the distal end of the elongate body than adjacent its proximal end.

Said groove or slot means may be wider adjacent said distal end than adjacent said proximal end.

A width of said fin means and a depth and a width of said groove or slot means may each vary evenly between said distal and proximal ends.

Preferably, said fin means are spaced equiangularly around a circumference of the operative head.

The groove or slot means will then also be spaced equiangularly.

Preferably, the operative head comprises at least four said fin means and at least four said groove or slot means.

Advantageously, the operative head comprises four helically-extending fin means spaced between four helically-extending groove or slot means.

In a preferred embodiment, a distal face of the operative head is concave.

Each fin means then projects distally at its distal end beyond a remainder of the operative head.

Advantageously, said distal face has a profile comprising a portion of a spherical surface.

Preferably, each groove or slot means has an arcuate cross-section.

Advantageously, each groove or slot means has a part-circular cross-section at each point along its length.

A radius of curvature of said part-circular cross-section may be constant along the length of each groove or slot means.

The operative head is preferably mounted at its proximal end to elongate waveguide means adapted to transmit ultrasonic vibrations.

Advantageously, the operative head and waveguide means have a common longitudinal axis.

The operative head may have an overall diameter greater than a diameter of the waveguide means.

The operative head may have an overall diameter up to twice the diameter of the waveguide means.

The fin means and the groove or slot means may extend continuously between the proximal and distal ends of the operative head.

The groove or slot means may have such a depth at the proximal end of the operative head that where the operative head meets the waveguide means, a floor of the groove or slot means coincides with an outer circumference of the waveguide means.

The operative head may have a substantially constant overall diameter, as defined by an outermost rim of each fin means, between its distal and proximal ends.

Each fin means may comprise transverse rim means at its outermost point.

Said transverse rim means may be defined between respective edges of the groove or slot means disposed to either side of said fin means.

Preferably, the operative head is adapted to be activated by torsional-mode ultrasonic vibrations.

According to a fifth aspect of the present invention, there is provided a surgical implement comprising a means to generate torsional-mode ultrasonic vibrations, elongate waveguide means adapted to transmit said ultrasonic vibrations extending therefrom, and end effector means so disposed at a distal end of the waveguide means as to be activatable by said ultrasonic vibrations, wherein the end effector means comprises an operative head as described in the first aspect above.

Preferably, said surgical implement is a surgical tool adapted to remove plastics material from within a cavity within a bone.

Advantageously, said surgical implement is a surgical tool adapted to cut bone, optionally cancellous bone.

Embodiments of the present invention will now be more particularly described, by way of example and with reference to the Figures of the accompanying drawings, in which.

Figure 1:
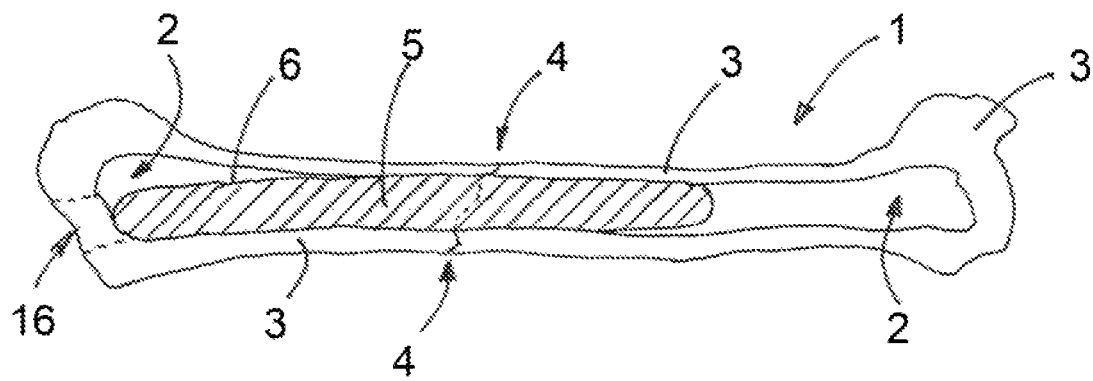
FIG. 1 is a longitudinal cross-sectional view of a fractured humerus bone provided with an internal plastics implant of known form reinforcing and aligning the fracture.

Referring now to the Figures and to FIG. 1 in particular, a humerus bone 1 is shown as an example of the elongate bones that may benefit from the internal fixation and reduction of fractures using polymeric implants or prostheses 5 formed in situ. The humerus 1 comprises an elongate axial cavity, the medullary cavity 2, enclosed by walls of substantially solid cortical bone 3. The cortical bone 3 is thicker at the ends of the humerus 1, forming articulating surfaces. In this case, a fracture 4 extends across a shaft of the humerus 1, intermediate between its ends.

The fracture 4 has been reduced (brought back into alignment) and fixated (internally "splinted") using a rigid plastics implant system as described in the introductory passages above. An aperture 16 has been formed in an end of the humerus 1, through the cortical bone 3, and a portion of the contents of the medullary cavity 2 has been removed. An elongate balloon 6 of a flexible plastics material, such as a polyester, has been introduced through the aperture 16 into the medullary cavity 2 and inflated so as to extend across the site of the fracture 4. Careful inflation, optionally with external manipulation, can ensure that the portions of the cortical bone 3 walls of the humerus 7 on each side of the fracture 4 are correctly aligned and mated together, with any cortical bone 3 fragments depressed or displaced into the medullary cavity 2 being returned to their correct position and alignment.

The elongate balloon 6 has then been filled with a photopolymerisable liquid, while ensuring that the fracture 4 remained reduced. An elongate light guide (not shown) was then introduced through the aperture 16 to extend generally along a longitudinal axis of the balloon 6, and light of the correct frequency to initiate photopolymerisation of the liquid was transmitted down the light guide into the liquid within the balloon 6. The liquid as a result polymerised to form a rigid plastics material. The light guide may be cut off or may be made from material that does not bond to the rigid plastics material, so that it may be withdrawn after use.

The rigid plastics material within the balloon 6 thus forms a rigid internal implant 5 extending across the fracture 4 and shaped to conform substantially to a profile of the medullary cavity 2, thus holding the fractured portion of the humerus 1 securely in position and preventing relative motion that might interfere with healing of the fracture 4. The diameter of the balloon 6 has been selected to approximate to that of the medullary cavity 2, and the implant 5 will correspond substantially to the internal profile of the cavity 2.

Once knitting of the fractured bone 3 is complete, or in the unlikely event of failure of the implant 5, it should be removed. The preferred approach is to re-open the aperture 16 and to introduce cutting/coring tools generally along a longitudinal axis of the implant 5 from its proximal end 15, removing the rigid plastics material from with the implant 5, known as "debulking" the implant 5. A series of tools of increasing size is used, ideally with each following a passage cut by the previous tool as a guide, so as gradually to core out the implant 5 until the remaining rigid plastics material is sufficiently undermined that it can be collapsed inwardly.

The balloon 6 may then be withdrawn through the aperture 16, bringing with it the collapsed remnants of the rigid plastics material. A replacement implant 5 may then be formed in situ, by the same method as described above, or the substantially healed humerus 1 may be left to complete the healing process.

It has been found, however, that passing these tools accurately down a desired axial path can be difficult. Additionally, a flap of skin and subcutaneous tissue must have been formed to permit access to the end of the humerus 1 to open up the window 16. However, in practice this flap closes very readily, making it difficult to access the window 16 or even to locate it.

Figure 2:
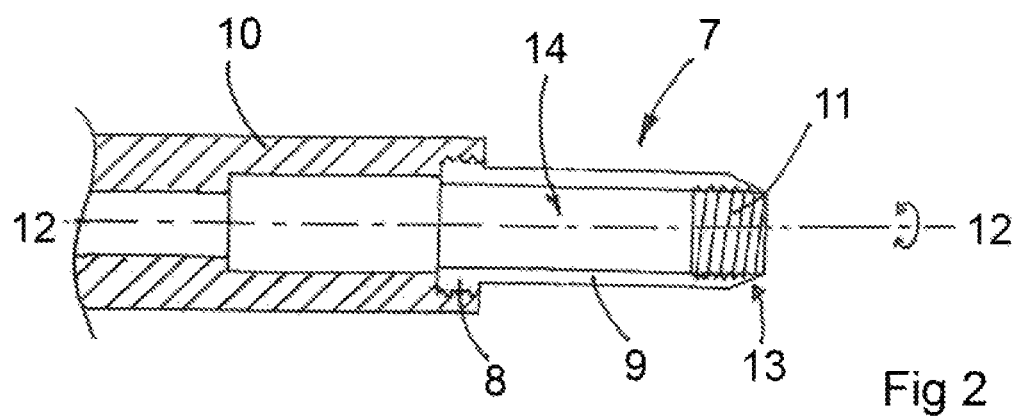
FIG. 2 is a longitudinal cross-sectional view of an access port embodying the present invention, mounted to an acoustic adaptor for transmission of ultrasonic vibrations thereto.
Figure 3:
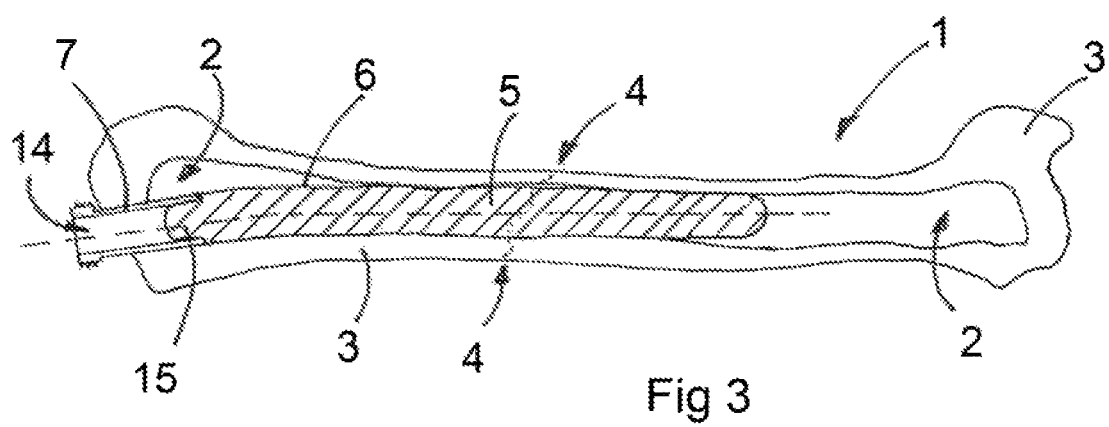
FIG. 3 is a longitudinal cross-sectional view of the humerus of FIG. 1 with the access port of FIG. 2 fitted thereto.

In the present invention, an access port 7 as shown in FIG. 2 is therefore provided, implanted into an end of the humerus 1 as shown in FIG. 3, both to guide the tools being used to debulk the implant 5 and to maintain free access to the aperture 16 and the implant 5 while the debulking procedure is performed.

The access port 7 comprises a hollow elongate cylindrical body 9, conveniently of stainless steel or ideally titanium. At a proximal end of the cylindrical body 9, there is an externally threaded portion 8, by which the access port 7 is detachably mountable to a corresponding acoustic adaptor 10 (details set out below). At a distal end of the cylindrical body 9, there is in this example an internally threaded portion 11 (function described below). In this example, but not all embodiments, there is also an external distal taper or bevelled zone 13 adjacent the distal end of the cylindrical body 9.

The acoustic adaptor 10 is in turn mounted to a source of torsional-mode ultrasonic vibrations (not shown), which may for example comprise a stack of piezo-electric ceramic elements mounted to a conversion horn, to which the acoustic adaptor 10 is mounted in turn. The acoustic adaptor 10 and the access port 7 are coaxially aligned, with their common longitudinal axis 12 being the torsional axis of these torsional mode ultrasonic vibrations. The acoustic adaptor 10 and access port 7 are dimensioned such that an anti-node of the torsional-mode ultrasonic vibrations is located at the distal end of the access port 7.

In use, the access port 7 is mounted to the acoustic adaptor 10 and introduced through the re-opened aperture 16 through the proximal end of the humerus 1, such that the distal end of the access port 7 contacts the proximal end 15 of the implant 5. The diameter of the hollow cylindrical body 9 of the access port 7 is chosen to match that of the implant 5 (which is restricted by the balloon 6 and by the cavity 2 walls), such that the hollow cylindrical body 9 would pass generally between the implant 5 and adjacent cortical bone 3 of the wall of the humerus 1 (or, where the medullary cavity 2 is substantially wider, such as adjacent each end of the humerus 1 shown in FIGS. 1 and 3, to pass between the implant 5 and adjacent tissues within the cavity 2).

When the access port 7 is ultrasonically vibrated, plastics material of the implant 5 adjacent the distal tip of the access port 7 becomes locally heated and may even partially depolymerise, softening as a result, thus allowing straightforward longitudinal insertion of the access port 7. In principle, such an access port 7 might simply be forced into position, with the distal tip of the access port 7 becoming wedged between the implant 5 and its surroundings. However, the use of ultrasonic vibrations to selectively soften the plastics material of the implant 5 should be much quicker and easier and much less traumatic.

Access ports 7 having a range of sizes will be provided. Access ports 7 with a diameter of about 15 mm or even 20 mm would be appropriate for use with implants in major bones such as the humerus 1, while for more slender bones such as ribs, access ports below 10 mm in diameter, even as small as 5 mm in diameter, would be appropriate.

Where the optional internal threaded portion 11 of the access port 7 is present, there is an additional benefit. The softened plastics material will readily conform to the threads of the internal threaded portion 11, anchoring the access port 7 securely to the proximal end 15 of the implant 5, once the ultrasonic vibrations have been turned off and the plastics material cools and sets solid once more. Other internal engagement structures may be used in place of the threaded portion 11, but threading is found to be particularly useful.

Once the access port 7 is fully in position, substantially aligned with the longitudinal axis of the implant 5, the ultrasonic vibrations are turned off. Once the plastics material of the implant 5 adjacent the access port 7 has re-solidified, the acoustic adaptor 10 is unscrewed from the access port 7 and withdrawn, leaving the access port 7 in position, as shown in FIG. 3.

The access port 7 thus defines a guide passage 14 leading to the proximal end 15 of the implant 5, and also serves to keep the flap of skin and tissue displaced, providing access and visibility to the implant 5. A surgeon may thus use the access port 7 to guide and align the tools being used to debulk the implant 5, from its axial region outwards, for example by sighting along the tool and through the guide passage 14. It should thus be possible to remove plastics material selectively from an interior of the implant 5, without significant risk of an operative tip of the tool penetrating the balloon 6 and contacting (and possibly damaging) surrounding bone 3.

The secure engagement between the re-solidified plastics material of the proximal end 15 of the implant 5 and structures such as the internally threaded portion 11 of the access port 7 (where present) may have a further benefit. To withdraw the balloon 6 and the collapsed remains of the implant 5 from the medullary cavity 2, a firm grip on a proximal end of the balloon 6 and/or on the proximal end 15 of the implant 5 is required. The threaded engagement between the access port 7 and the proximal end 15 of the implant 5, with the balloon 6 almost certainly fused or caught in between, should provide a secure anchoring point. A tool mounted to the proximal end of the access port 7, for example engaged with the externally threaded portion 8, would allow sufficient longitudinal force to be applied to free any remaining adhesion between the remains of the implant 5 and its surroundings and to draw out all remaining foreign material from within the medullary cavity 2, allowing the humerus 1 to complete unhindered healing.

Figure 4:
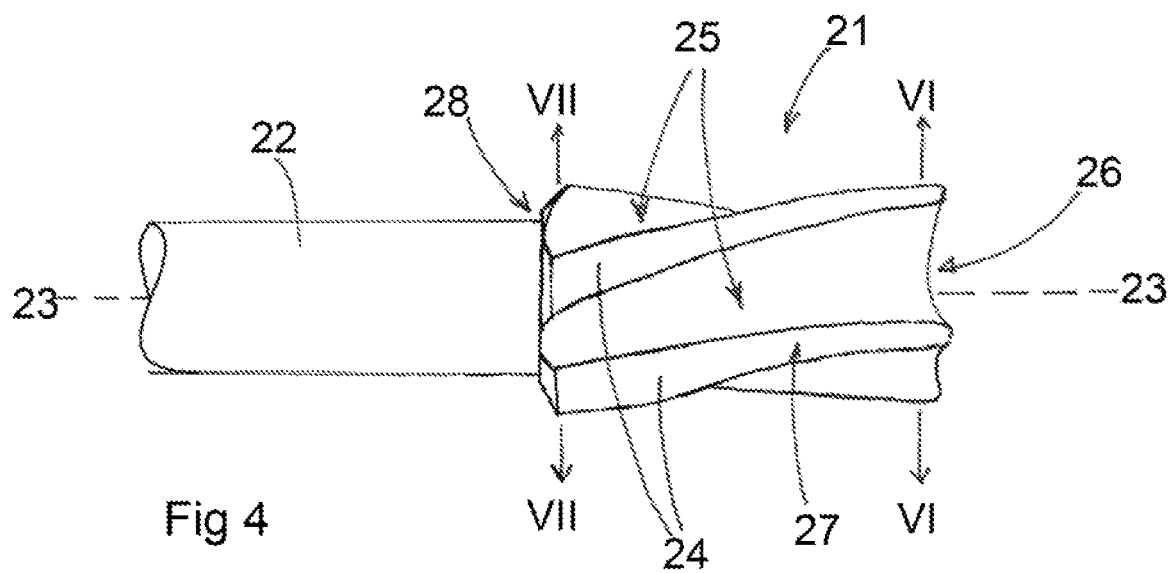
FIG. 4 is a side elevation of an operative head of a surgical tool embodying the present invention.

Referring now to FIGS. 4 to 7, and to FIG. 4 in particular, there is shown an operating head or end-effector 21 of the ultrasonically-vibratable surgical implement. The operating head 21 is coaxially mounted to a distal end of an elongate cylindrical waveguide 22, which typically extends from a hand piece (not shown) manipulable by a surgeon. The waveguide 22 is connected at its proximal end to an ultrasound generator, typically via a conversion horn of known form. In this invention, the ultrasound generator operates in torsional mode. Torsional-mode ultrasonic vibrations about their mutual longitudinal axis 23 are thus induced in the waveguide 22 and the operating head 21. The ultrasonic system is tuned by known methods such that a resonant standing wave is set up within the generator, waveguide 22 and operative head 21, an antinode of the wave (i.e. maximum vibrational amplitude) being located at or immediately adjacent a distal tip of the operative head 21.

The operative head 21 here comprises four symmetrically-spaced ribs, ridges or fins 24, extending radially outwardly with respect to the longitudinal axis 23. These fins 24 are separated by four symmetrically-spaced slots, channels or grooves 25, each fin 24 being defined between a pair of adjacent grooves 25.

The ribs/fins 24 and grooves 25 all extend helically between a distal end 26 and a proximal end 28 of the operative head 21. Each rib/fin 24 tapers gradually towards the distal end 26 of the operative head 21, being significantly broader adjacent the proximal end 28 than the distal end 26. Conversely, each groove 25 is broader and deeper at the distal end 26 of the operative head 21, gradually becoming shallower and narrower towards the proximal end 28.

The distal end 26 of the operative head 21 has a concave profile. In this embodiment, this profile of the distal end 26 comprises part of a spherical surface, thus forming a distally-oriented bowl or dish, coaxially aligned with the operative head 21 and waveguide 22. As a result, an outermost distal tip of each fin 24 extends further, distally of the operative head 21, than does a remainder of the distal end 26.

This has an effect on the operation of the operative head 21. Torsional mode vibrations, comprising angular displacements about the axis 23, thus have a linear displacement amplitude that varies with radial distance outwards from the axis 23. The distal tips of the fins 24 are thus the most highly energised or activated parts of the operative head 21, while the amplitude of vibration falls away towards a floor of each groove 25. Plastics materials depolymerised and/or melted by contact with the fins 24 will flow to and along the grooves 25, and then away from the proximal end 28 of the operative head 21. (NB: it is believed that the helical form of the grooves 25 and the fins 24 has further beneficial effects currently under investigation).

Figure 5:
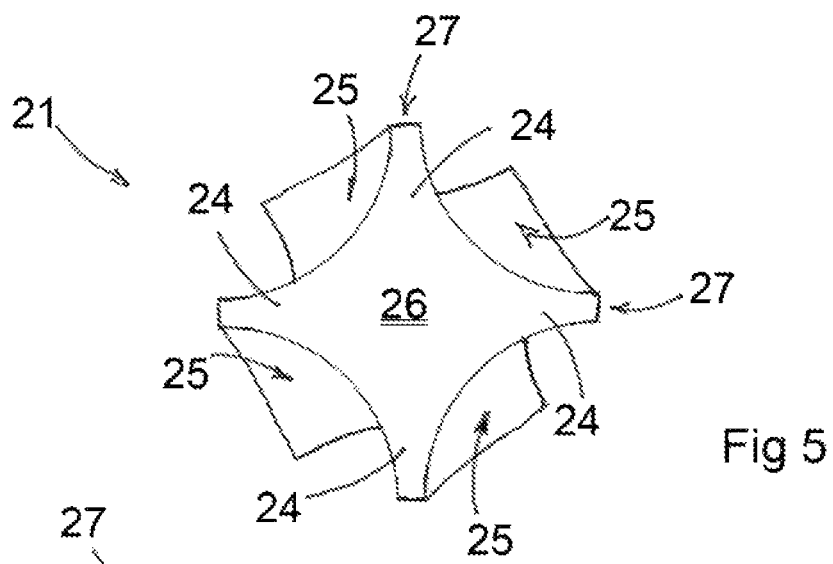
FIG. 5 is a distal end elevation of the operative head of FIG. 4.

FIG. 5 shows an end elevation of the distal end 26 of the operative head 21. In this view, the four fins 24 defined between the four grooves 25 can more clearly be seen, as can the helical alignment of the grooves 25, corkscrewing back towards the proximal end 28 of the operative head 21.

FIG. 5 also shows the preferred profile of the grooves 25, which is arcuate, ideally part-circular. In this embodiment, the radius of curvature of this profile remains constant, while the overall groove 25 depth reduces gradually towards the proximal end 28, which also results in the overall breadth of the groove 25 lessening.

Figure 6:
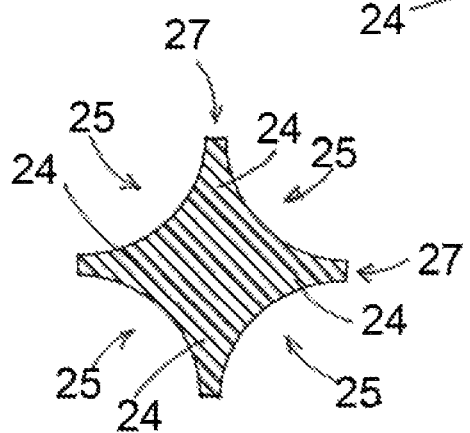
FIG. 6 is a radial cross-section of the operative head of FIG. 4, taken along the line VI-VI adjacent its distal end.
Figure 7:
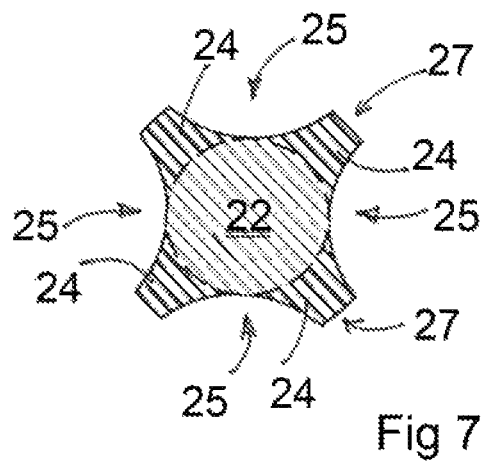
FIG. 7 is a radial cross-section of the operative head of FIG. 4, taken along the line VII-VII adjacent its proximal end.

This is shown in more detail in FIGS. 6 and 7, which are radial cross-sections (NB: not cross-sectional views) of the operative head 21, taken adjacent its distal end 26 and proximal end 28 respectively.

In FIG. 6, the four part-circular grooves 25 extend deep into the operative head 21, leaving four relatively narrow fins 24 upstanding between them. It should be noted that the grooves 25 do not meet at their peripheries, which would form a hypocycloid profile. Each fin, ridge or rib 24 has a narrow, flat crest or rim 27 at its radially outermost point. (NB: the operative head 21 is not intended to have any macroscopically "sharp" edges, with the result that it may be safely manipulated in confined spaces, and only acts on surrounding tissues when activated by ultrasonic vibrations).

In FIG. 7, by contrast, nearer the proximal end of the operative head 21, the depths of the grooves 25 are significantly reduced relative to those shown in FIG. 6, as are their widths. The fins 24 remain well-defined, but they are clearly broader at this point (compare the widths of the respective rims 27 shown in FIGS. 6 and 7). In this embodiment, the floors of the grooves 25 are arranged to emerge from the proximal end 28 of the operative head 21 level with an outer surface of the waveguide 22 (as shown by circular feature 22 of FIG. 7, representing the adjoining waveguide 22).

In FIGS. 6 and 7, the fins 24 and grooves 25 are represented as having rotated by forty-five degrees anti-clockwise along their helical paths, measured from the distal end 26, (shown in FIG. 6) to the proximal end 28 of the operative head 21 (FIG. 7). This is one example of how tight the helical curves used may be, but significant variation in the sharpness of the "twist" of the fins 24/grooves 25 is envisaged as being practicable.

In practice, the waveguide 22 and operative head 21 may be milled from a single blank of titanium or the like. The operative head 21 may conveniently be formed from a coaxial cylindrical blank located at the distal end of the waveguide 22, having an overall diameter of up to 100% greater than that of the narrow cylindrical waveguide 22 itself.

The rims 27 of the fins 24 then represent a vestigial remnant of an outer surface of the cylindrical blank, after the helical grooves 25 have been cut into it. The reduction in depth and width of the grooves 25 between their distal and proximal ends results in the rims 27 of the fins 24 increasing in width by between 50% and 100% from their respective distal to proximal ends.

A typical example of such an operative head 21 may be from four to eight millimetres long, measured linearly between its proximal 28 and distal 26 ends. Although there may be some variation, the general proportions of the operative head 21 shown in the Figures are currently believed to be representative.

The above description concentrates on the use of the operative head 21 for removal of plastics material from within a bone cavity. Mounted distally to a torsionally-vibratable ultrasonic surgical tool, the operative head 21 is aligned with the proximal end 15 of the implant 5 by insertion through the guide passage 14 of the access port 7. The distal end 26 of the operative head 21 is presented to the proximal end 15 of the implant 5 and the operative head 21 is activated ultrasonically. Particularly at the distal tips of the distal end 26, this both transfers energy into the plastics material of the implant 5, potentially producing at least a degree of softening, and it can directly cut into the plastics material of the implant 5. As the operative head 21 is pushed longitudinally along the implant 5, guided by the access port 7, softened plastics material and entrained plastics fragments will travel down the grooves 25 to and out from the proximal end 28 of the operative head 21. When the ultrasonic vibrations are turned off, this material will re-solidify, at least partially, and can be scraped out of the interior of the implant 5 by retroactive proximal motions of the operative head 21 of using other tools. If a single passage of the operative head 21 does not lead to the implant 5 being hollowed out enough to collapse inwardly, then the hollowing can continue with further passages along slightly different axes or by passing an operative head of greater overall diameter along the passage created by the first, enlarging the passage diameter and undermining the outer layers of the implant 5 further.

The rims 27 of the fins 24 can also be used as a cutting edge. Although the resonant torsional vibration will be at its maximum amplitude at the distal tip of the operative head 21, the surface of each rim 27 of a fin 24 will still be activated, lessening proximally along the operative head 21. A side of the operative head 21 near its distal end 26 may thus be move laterally into contact with material to be cut, for example to enlarge a passage beyond the diameter of the operative head 21 itself or to trim locally. (NB: although the operative head 21 has a passing resemblance to a router bit of a macroscopic drill, the mode of action is different—a router bit is rotated continuously in a single direction, while the operative head 21 of the present invention is rotated back and forth at a very high, ultrasonic frequency oscillatory motion having a relatively short "stroke length"; also, the main action of a router bit is lateral to the rotational axis, while these tools operate primarily linearly along this rotational axis).

Additionally, although the operative head 21 is mainly envisaged as acting on plastics materials, it will also be effective in cutting bone, particularly cancellous bone, should there have been bone intergrowth with an implant. While this is not likely with the exactly internal implants described above, there are a wide range of other implants for fixations of fractures and the like where the operative heads described could well laso be usable. For example, there are known methods for freeing the shaft of a femoral implant of a replacement hip-joint from its surrounding bone cement during revision. However, it will still be necessary to remove the bone cement and any bone ingrowth from within the femur, before fresh cement and a replacement implant are inserted. Operative heads such as those described are believed to be effective for removing the cement by following the gap left by the shaft with a wider operative head 21, which can also cut away any ingrowing bone and may also be used laterally to trim the cavity by its action on cortical bone of the femoral wall, where necessary.

The operative heads 21 described are thus a highly effective part of the tool kit for removal or revision of internally-formed plastics intraosteal implants/prostheses and are also useful for a range of other prosthesis removal and revision procedures.

The invention claimed is:

1. Apparatus for removal or revision of an internal plastics implant extending longitudinally within an elongate bone cavity of a hollow bone, comprising an operative head for an ultrasonically-vibratable surgical tool, said operative head comprising an elongate body of substantially cylindrical symmetry, having a proximal end and a distal end, said elongate body comprising at least three elongate, radially-outstanding helically-extending fins, each fin extending between said proximal and distal ends of the elongate body wherein said fins taper in width, being broader adjacent the proximal end of the elongated body than adjacent the distal end of the elongated body, and a corresponding number of helically-extending grooves also extending between said proximal and distal ends, each said fin being defined between a neighboring pair of said grooves, and said operative head further comprising a distal face, said distal face being concave.

2. The apparatus as claimed in claim 1, wherein said grooves are deeper adjacent the distal end of the elongate body than adjacent the proximal end of the elongate body.

3. The apparatus as claimed in claim 1, wherein said grooves are wider adjacent the distal end of the elongate body than adjacent the proximal end of the elongate body.

4. The apparatus as claimed in claim 1, wherein each said groove has an arcuate cross-section.

5. The apparatus as claimed in claim 1, wherein the operative head is mounted at its proximal end to an elongate waveguide adapted to transmit ultrasonic vibrations.

6. The apparatus as claimed in claim 5, wherein the operative head has an overall diameter greater than a diameter of the elongate waveguide up to twice said diameter of the elongate waveguide.

7. The apparatus as claimed in claim 1, comprising:
a surgical implement comprising a means to generate torsional-mode ultrasonic vibrations,
an elongate waveguide adapted to transmit said torsional-mode ultrasonic vibrations and having a proximal end and a distal end, said elongate waveguide extending away from said means to generate torsional-mode ultrasonic vibrations, and
the operative head being so disposed at said distal end of the elongate waveguide as to be activatable by said torsional-mode ultrasonic vibrations.

8. Apparatus for removal or revision of an internal plastics implant extending longitudinally within an elongate bone cavity within a hollow bone, comprising an access port device and a tool for inserting said access port device into the bone, wherein said tool comprises a source of ultrasonic vibrations, said ultrasonic vibrations comprising torsional-mode ultrasonic vibrations, wherein the torsional-mode ultrasonic vibrations inhibit a distal extensional drilling effect on the internal plastics implant and elongate bone cavity, and wherein said access port device comprises a hollow cylindrical body extending between an open proximal end and an open distal end, the hollow cylindrical body comprising adjacent its proximal end a mounting adapted to mount the access device detachably to said source of ultrasonic vibrations, and wherein a distal portion of said hollow cylindrical body is insertable through an aperture formed in a wall of the hollow bone into said elongate bone cavity so that said distal portion surrounds a proximal portion of the internal plastics implant, with a longitudinal axis of the hollow cylindrical body being substantially coaxially aligned with a longitudinal axis of the internal plastics implant.

9. The apparatus as claimed in claim 8, wherein said distal portion of the hollow cylindrical body is locatable between said proximal portion of the internal plastics implant and an inner surface of the elongate bone cavity adjacent said proximal portion of the internal plastics implant.

10. The apparatus as claimed in claim 8, wherein an inner surface of said distal portion of the hollow cylindrical body is profiled to engage with the plastics material of the internal plastics implant.

11. The apparatus as claimed in claim 10, wherein said inner surface of the distal portion of the hollow cylindrical body comprises an internal screw thread.

12. The apparatus as claimed in claim 8, wherein the hollow cylindrical body comprises, at its proximal end, a means of engagement by which the hollow cylindrical body is detachably mountable to the source of ultrasonic vibrations of the tool, said means of engagement comprising an external screw thread extending around an outer surface of the hollow cylindrical body adjacent its proximal end, adapted to engage with a cooperating screw thread on the source of ultrasonic vibrations.

13. The apparatus as claimed in claim 12, wherein the access port device is so dimensioned that an antinode of resonant ultrasonic vibrations from the source of ultrasonic vibrations is located adjacent the distal end of the hollow cylindrical body.

14. The apparatus as claimed in claim 8, wherein the tool for inserting an access port device into a hollow bone is so configured and dimensioned that an antinode of ultrasonic vibrations from said source of ultrasonic vibrations is located adjacent the distal end of the hollow cylindrical body of the access port device.

15. A method for revising an internal plastics implant extending longitudinally within an elongate bone cavity within a hollow bone, comprising the steps of providing apparatus as claimed in claim 8; mounting the access port device of said apparatus to the source of ultrasonic vibrations of the tool of said apparatus; inserting a distal portion of the hollow cylindrical body of said access port device through an aperture formed in the hollow bone so that said distal portion extends around a proximal portion of the internal plastics implant, with a longitudinal axis of the hollow cylindrical body being substantially coaxially aligned with a longitudinal axis of the internal plastics implant; passing a cutting tool through the hollow cylindrical body, in alignment therewith; and operating said cutting tool so as to remove plastics material from a generally axial region of the internal plastics implant.

16. The method as claimed in claim 15, wherein said source of ultrasonic vibrations is operated during said step of inserting of the access port device so as to cause the hollow cylindrical body of the access port device to vibrate ultrasonically, thus softening adjacent plastics material of the internal plastics implant to facilitate said step of inserting.

17. Apparatus for removal or revision of an internal plastics implant extending longitudinally within an elongate bone cavity of a hollow bone, comprising an operative head for an ultrasonically-vibratable surgical tool, said operative head comprising:
- an elongate body of substantially cylindrical symmetry, having a proximal end and a distal end, said elongate body comprising at least three elongate, radially-outstanding helically-extending fins, each fin extending between said proximal and distal ends of the elongate body, and
- a corresponding number of helically-extending grooves also extending between said proximal and distal ends, each said fin being defined between a neighboring pair of said grooves, and said operative head further comprising a distal face, said distal face being concave,
- wherein the operative head is mounted at its proximal end to an elongated waveguide adapted to transmit ultrasonic vibrations.

18. The apparatus as claimed in claim 17, wherein the operative head has an overall diameter greater than a diameter of the elongate waveguide up to twice said diameter of the elongate waveguide.

\* \* \* \* \*